US008620429B2

(12) United States Patent
Li et al.

(10) Patent No.: US 8,620,429 B2
(45) Date of Patent: *Dec. 31, 2013

(54) METHOD AND APPARATUS FOR CONCURRENT ATRIO-VENTRICULAR ANTI-TACHYCARDIA PACING

(75) Inventors: Dan Li, Shoreview, MN (US); Jaeho Kim, Redmond, WA (US); Joseph M. Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/457,630

(22) Filed: Apr. 27, 2012

(65) Prior Publication Data

US 2012/0215273 A1  Aug. 23, 2012

Related U.S. Application Data

(63) Continuation of application No. 12/234,840, filed on Sep. 22, 2008, now Pat. No. 8,170,669.

(60) Provisional application No. 60/978,972, filed on Oct. 10, 2007.

(51) Int. Cl.
*A61N 1/39* (2006.01)

(52) U.S. Cl.
USPC .......................................................... 607/14

(58) Field of Classification Search
None
See application file for complete search history.

(56) References Cited

U.S. PATENT DOCUMENTS

| | | | |
|---|---|---|---|
| 4,998,974 A | 3/1991 | Aker | |
| 6,708,058 B2 | 3/2004 | Kim et al. | |
| 7,162,300 B2 | 1/2007 | van Groeningen et al. | |
| 7,206,633 B2 | 4/2007 | Saba | |
| 7,873,414 B2 | 1/2011 | Dong et al. | |
| 7,970,468 B1 | 6/2011 | Ostrow | |
| 2004/0172067 A1 | 9/2004 | Saba | |
| 2005/0149125 A1 | 7/2005 | Kim et al. | |
| 2006/0217769 A1 | 9/2006 | Saba | |
| 2007/0135848 A1 | 6/2007 | Kim et al. | |
| 2007/0142866 A1 | 6/2007 | Li | |
| 2007/0173894 A1 | 7/2007 | Li | |
| 2007/0191894 A1 | 8/2007 | Li | |

(Continued)

OTHER PUBLICATIONS

Free Online dictionary definition of synchronously http://www.thefreedictionary.com/synchronized.*

(Continued)

*Primary Examiner* — Carl H Layno
*Assistant Examiner* — Paula J Stice
(74) *Attorney, Agent, or Firm* — Schwegman Lundberg & Woessner, P.A.

(57) ABSTRACT

An implantable medical device delivers anti-tachyarrhythmia therapies including anti-tachycardia pacing (ATP). If a detected tachyarrhythmia is classified as a type suitable for treatment using ATP, the implantable medical device selects one of an atrial ATP (A-ATP) mode, a ventricular ATP (V-ATP) mode, and a concurrent atrio-ventricular ATP (concurrent AV-ATP) mode according to the characteristics of the detected tachyarrhythmia. The concurrent ATP mode is an ATP mode during which the atrial pacing pulses and the ventricular pacing pulses are delivered concurrently. In one embodiment, the concurrent AV-ATP mode includes a synchronized atrio-ventricular ATP (synchronized AV-ATP) mode during which atrial and ventricular pacing pulses are delivered synchronously and an independent atrio-ventricular ATP (independent AV-ATP) mode during which atrial and ventricular pacing pulses are delivered concurrently but timed independently.

18 Claims, 9 Drawing Sheets

(56) References Cited

U.S. PATENT DOCUMENTS

| | | |
|---|---|---|
| 2007/0197928 A1 | 8/2007 | Kim et al. |
| 2007/0260283 A1 | 11/2007 | Li |
| 2007/0282381 A1 | 12/2007 | Li |
| 2008/0183228 A1 | 7/2008 | Kim et al. |
| 2009/0099616 A1 | 4/2009 | Li et al. |

OTHER PUBLICATIONS

"U.S. Appl. No. 12/234,840, Examiners Interview Summary mailed Nov. 8, 2011", 3 pgs.

"U.S. Appl. No. 12/234,840, Non Final Office Action mailed Aug. 10, 2011", 10 pgs.

"U.S. Appl. No. 12/234,840, Notice of Allowance mailed Dec. 29, 2011", 8pgs.

"U.S. Appl. No. 12/234,840, Response filed Nov. 10, 2011 to Non Final Office Action mailed Aug. 10, 2011", 14 pgs.

Saba, S., et al., "New method for real-time discrimination and management of ventricular and supraventricular tachyarrhythmias applicable to patients with dual-chamber cardioverter-defibrillators", Am J Cardiol., 93(1), (2004), 111-4.

Saba, S., et al., "Simultaneous atrial and ventricular anti-tachycardia pacing as a novel method of rhythm discrimination.", J. Cardiovasc Electrophysiol., 17(7), (2006), 695-701.

\* cited by examiner

METHOD AND APPARATUS FOR CONCURRENT ATRIO-VENTRICULAR ANTI-TACHYCARDIA PACING

CLAIM OF PRIORITY

This application is a continuation of U.S. patent application Ser. No. 12/234,840, filed Sep. 22, 2008, now issued as U.S. Pat. No. 8,170,669, which claims the benefit under 35 U.S.C. 119(e) of U.S. Provisional Patent Application Ser. No. 60/978,972, entitled "Method and Apparatus for Concurrent Atrio-Ventricular Anti-Tachycardia Pacing," filed Oct. 10, 2007, each of which are incorporated herein by reference in its entirety.

TECHNICAL FIELD

This document relates generally to cardiac rhythm management (CRM) systems and particularly to a system providing for anti-tachycardia pacing (ATP), including concurrent delivery of ATP to both atrial and ventricular chambers.

BACKGROUND

Tachyarrhythmias are abnormal heart rhythms characterized by a rapid heart rate. Tachyarrhythmia generally includes supraventricular tachyarrhythmia and ventricular tachyarrhythmia. Fibrillation is a form of tachyarrhythmia further characterized by an irregular heart rhythm. In a normal heart, the sinoatrial (SA) node, the heart's predominant natural pacemaker, generates electrical impulses, called action potentials, that propagate through an electrical conduction system to the atria and then to the ventricles of the heart to excite the myocardial tissues. The atria and ventricles contract in the normal atrio-ventricular sequence and synchrony to result in efficient blood-pumping functions indicated by a normal hemodynamic performance. Ventricular tachyarrhythmia occurs when the electrical impulses propagate along a pathologically formed self-sustaining conductive loop within the ventricles or when a biologic pacemaker (focus) in a ventricle usurps control of the heart rate from the SA node. When the atria and the ventricles become dissociated during ventricular tachyarrhythmia, the ventricles may contract before they are properly filled with blood, resulting in diminished blood flow throughout the body. This condition becomes life-threatening when the brain is deprived of sufficient oxygen supply. Ventricular fibrillation (VF), in particular, stops blood flow within seconds and, if not timely and effectively treated, causes immediate death. In very few instances a heart recovers from VF without treatment.

Ventricular cardioversion and defibrillation are used to terminate most ventricular tachyarrhythmias, including ventricular tachycardia (VT), and VF. An implantable cardioverter/defibrillator (ICD) is a CRM device that delivers cardioversion/defibrillation pulses, each being an electric shock, to terminate a detected tachyarrhythmia episode by depolarizing the entire myocardium simultaneously and rendering it refractory.

Another type of electrical therapy for tachyarrhythmia is ATP, including atrial ATP for treating atrial tachyarrhythmia and ventricular ATP for treating ventricular tachyarrhythmia. In ATP, the heart is competitively paced in an effort to interrupt the reentrant loop causing the tachyarrhythmia. In an ICD that includes ATP and cardioversion/defibrillation capabilities, the efficacy of each available anti-tachyarrhythmia therapy depends on the type and origin of the tachyarrhythmia. For example, a ventricular anti-tachycardia pacing therapy is generally ineffective in terminating an atrial tachyarrhythmia. Additionally, the delivery of each cardioversion/defibrillation pulse consumes a considerable amount of power and results in patient discomfort owing to the high voltage of the shock pulses. If delivered during the atrial vulnerable period, a cardioversion/defibrillation pulse may also cause atrial fibrillation. Therefore, for therapy efficacy, device longevity, and patient satisfaction, it is desirable for an ICD to use ATP to terminate a detected tachyarrhythmia wherever possible. For this and other reasons, there is a need for expanding the capability and improving the effectiveness of ATP in terminating tachyarrhythmias.

SUMMARY

An implantable medical device delivers anti-tachyarrhythmia therapies including anti-tachycardia pacing (ATP). If a detected tachyarrhythmia is classified as a type suitable for treatment using ATP, the implantable medical device selects one of an atrial ATP (A-ATP) mode, a ventricular ATP (V-ATP) mode, and a concurrent atrio-ventricular ATP (concurrent AV-ATP) mode according to the characteristics of the detected tachyarrhythmia. The concurrent ATP mode is an ATP mode during which the atrial pacing pulses and the ventricular pacing pulses are delivered concurrently. In one embodiment, the concurrent AV-ATP mode includes a synchronized atrio-ventricular ATP (synchronized AV-ATP) mode during which atrial and ventricular pacing pulses are delivered synchronously and an independent atrio-ventricular ATP (independent AV-ATP) mode during which atrial and ventricular pacing pulses are delivered concurrently but timed independently.

In one embodiment, an implantable cardiac rhythm management (CRM) device includes a pacing circuit, a tachyarrhythmia detection and classification circuit, and an ATP control circuit. The pacing circuit delivers atrial pacing pulses and ventricular pacing pulses. The tachyarrhythmia detection and classification circuit includes a cardiac sensing circuit, a rate detector, a tachyarrhythmia detector, and a tachyarrhythmia classifier. The cardiac sensing circuit senses cardiac signals indicative of atrial depolarizations and ventricular depolarizations. The rate detector detects an atrial rate and a ventricular rate using the cardiac signals. The tachyarrhythmia detector detects tachyarrhythmia using the ventricular rate and one or more tachyarrhythmia threshold rates. The tachyarrhythmia classifier classifies the detected tachyarrhythmia. The ATP control circuit controls delivery of one or more of the atrial pacing pulses and the ventricular pacing pulses according to a selected ATP mode and includes an ATP mode selector. The ATP mode selector selects one of the A-ATP mode, V-ATP mode, and concurrent AV-ATP mode using one or more specified ATP mode selection criteria and the classification of the detected tachyarrhythmia.

In one embodiment, a method for operating an implantable CRM device is provided. Cardiac signals indicative of atrial depolarizations and ventricular depolarizations are sensed. An atrial rate and a ventricular rate are detected using the cardiac signals. Tachyarrhythmia is detected using the ventricular rate and one or more tachyarrhythmia threshold rates. The detected tachyarrhythmia is classified. An ATP mode is selected from the A-ATP mode, V-ATP mode, and concurrent AV-ATP mode using one or more specified ATP mode selection criteria and the classification of the detected tachyarrhythmia. Delivery of one or more of atrial pacing pulses and the ventricular pacing pulses are controlled according to the selected ATP mode.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
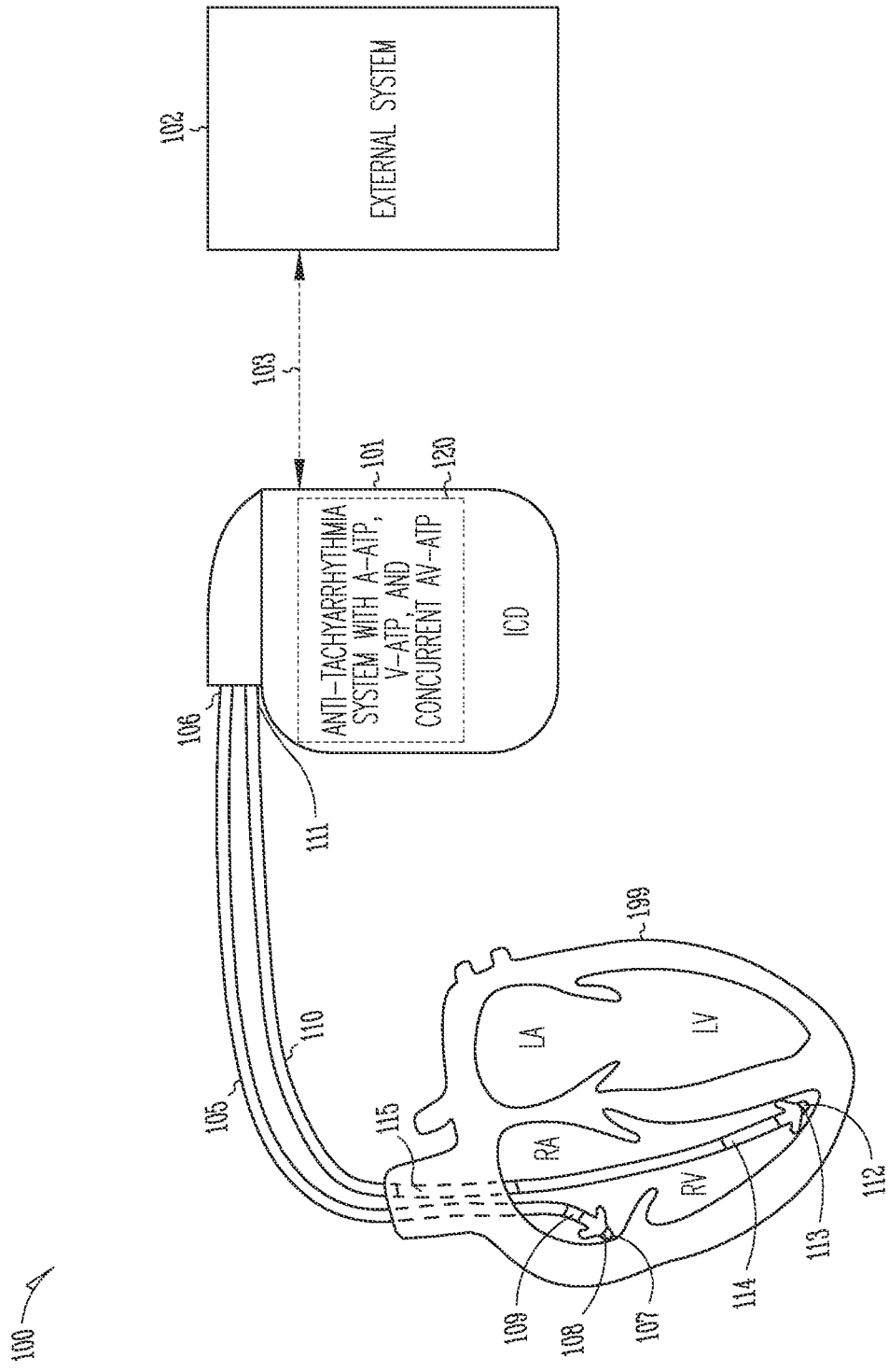
FIG. 1 is an illustration of an embodiment of a CRM system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length (also known as ventricular interval) falls below a tachyarrhythmia threshold interval. The appended claims should be construed to cover such variations.

In this document, a "fast beat" refers to a heart beat having a heart rate that falls into a tachyarrhythmia detection zone, which is typically defined by at least one tachyarrhythmia detection threshold, and a "slow beat" refers to a heart beat having a heart rate that is below the tachyarrhythmia detection zone. In other words, a "fast beat" is a heart beat having a tachyarrhythmic heart rate, and a "slow beat" is a heart beat having a heart rate that is not tachyarrhythmic.

In this document, "atrial ATP (A-ATP) mode" refers to an ATP mode during which only atrial pacing pulses are delivered, "ventricular ATP (V-ATP) mode" refers to an ATP mode during which only ventricular pacing pulses are delivered, and "concurrent atrio-ventricular ATP (concurrent AV-ATP) mode" refers to an ATP mode during which atrial and ventricular pacing pulses are concurrently delivered. The concurrent AV-ATP mode includes two specific modes of operation: "independent atrio-ventricular ATP (independent AV-ATP) mode" and "synchronized atrio-ventricular ATP (AV-ATP) mode". During the independent AV-ATP mode, atrial and ventricular pacing pulses are delivered concurrently but not necessarily synchronously. During the synchronized AV-ATP mode, atrial and ventricular pacing pulses are delivered approximately simultaneously or with a synchronization offset. In various embodiments, the synchronization offset is programmable and/or dynamically adjustable.

This document discusses, among other things, an ICD that delivers anti-tachyarrhythmia therapies including ATP. Available ATP operation modes include A-ATP mode, V-ATP mode, and concurrent AV-ATP mode. In response to a detection of tachyarrhythmia, the ICD classifies the tachyarrhythmia and selects an anti-tachyarrhythmia therapy. If ATP is selected, the ICD further selects one of the ATP operation modes according to the classification and various detected characteristics of the detected tachyarrhythmia. The concurrent AV-ATP mode is selected, for example, when the detected tachyarrhythmia has characteristics indicative of an origin in atria, atrio-ventricular node, or ventricular basal (high-septal) areas (i.e., ventricular regions close to atria) or a reentrant loop that covers at least an atrium and a ventricle. In such examples, the detected tachyarrhythmia may be difficult to classify with high certainty, but likely to be terminated by pacing on the concurrent AV-ATP mode. In one scenario, AF with short stable periods, fast ventricular response, and a waveform marginally correlated to a normal sinus rhythm waveform may be detected as VT, but pacing at the V-ATP mode is unlikely to terminate AF. In another scenario, it may be difficult to determine whether a 1:1 tachyarrhythmia (in which atrial and ventricular rates are approximately equal) is a VT with retrograde conduction or a supraventricular tachycardia (SVT) with fast ventricular response, so pacing at either the V-ATP mode or the A-ATP mode may not be effective. Pacing at the concurrent AV-ATP mode in such scenarios improves the effectiveness of the ATP therapy by bypassing the difficulty or uncertainty associated with the classification of the detected tachyarrhythmia. The concurrent mode further includes independent AV-ATP mode and synchronized AV-ATP mode. The synchronized AV-ATP mode is selected when a synchronized delivery of atrial and ventricular pacing pulses is feasible, such as during the 1:1 tachyarrhythmia. The independent AV-ATP mode is selected when a synchronized delivery of atrial and ventricular pacing pulses is difficult or impossible to control, such as when the atrial rate is substantially higher than the ventricular rate. During the synchronized AV-ATP mode, the delivery of the atrial pacing pulses and the delivery of the ventricular pacing pulses are synchronized. During the independent AV-ATP mode, the delivery of the atrial pacing pulses and the delivery of the ventricular pacing pulses are independently timed.

FIG. 1 is an illustration of an embodiment of a CRM system 100 and portions of the environment in which CRM system 100 operates. CRM system 100 includes an ICD 101 that is electrically coupled to a heart 199 through leads 105 and 110. An external system 102 communicates with ICD 101 via a telemetry link 103.

ICD 101 is an implantable medical device that performs CRM functions including delivery of cardiac pacing and cardioversion/defibrillation therapies. ICD 101 includes a hermetically sealed can housing an electronic circuit that senses physiological signals and delivers therapeutic electrical pulses. The hermetically sealed can may also function as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is typically a pacing lead that includes a proximal end 106 connected to ICD 101 and a distal end 107 placed in the right atrium (RA) of heart 199. A pacing-sensing electrode 108 is located at distal end 107. Another pacing-sensing electrode 109 is located near distal end 107. Electrodes 108 and 109 are electronically connected to ICD 101 via separate conductors in lead 105 to allow for sensing of the atrial electrogram and/or delivery of atrial pacing pulses. Lead 110 is typically a defibrillation lead that includes a proximal end 111 connected to ICD 101 and a distal end 112 placed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to ICD 101 via separate conductors in lead 110. Electrode 113 and 114 allow for sensing of the ventricular electrogram and/or delivery of ventricular pacing pulses. Electrodes 114 and 115 allow for delivery of ventricular cardioversion/defibrillation pulses. The functions of these electrodes are discussed above by way of example and not by way of limitation. Other ways of using these electrodes are possible as understood by those of skill in the art.

ICD 101 includes an anti-tachyarrhythmia system 120 providing for anti-tachyarrhythmia therapies including ATP therapies in the A-ATP mode, V-ATP mode, or concurrent AV-ATP mode. The A-ATP mode includes delivery of atrial pacing pulses. The V-ATP mode includes delivery of ventricular pacing pulses. The concurrent AV-ATP mode includes concurrent delivery of atrial and ventricular pacing pulses. Two specific concurrent AV-ATP modes are synchronized AV-ATP mode and independent AV-ATP mode. Synchronized AV-ATP mode includes delivery of atrial and ventricular pacing pulses in a synchronized manner. Independent AV-ATP mode includes concurrent delivery of atrial and ventricular pacing pulses with the delivery of pacing pulses to each chamber independently timed. In response to a detected tachyarrhythmia episode, ICD 101 analyzes the sensed atrial and ventricular electrograms to classify and characterize the tachyarrhythmia. If the detected tachyarrhythmia is classified as a type suitable for an ATP therapy, one of the A-ATP mode, V-ATP mode, and concurrent AV-ATP mode is selected using the classification and characteristics of the tachyarrhythmia. In various embodiments, the concurrent AV-ATP mode improves the efficacy of ATP when compared to single-chamber ATP modes, especially when the reentrant circuit of the tachyarrhythmia loops in both atrial and ventricular chambers or when it is difficult to locate the origin of the tachyarrhythmia with a satisfactory level of certainty. In one embodiment, one of the synchronized AV-ATP mode and independent AV-ATP mode is selected as the concurrent AV-ATP mode based on whether synchronization between the atrial pacing pulses and the ventricular pacing pulses is feasible. Anti-tachyarrhythmia system 120 is further discussed below, with references to FIGS. 2-9.

External system 102 allows for programming of ICD 101 and receives signals acquired by ICD 101. In one embodiment, external system 102 includes a programmer. In another embodiment, external system 102 is a patient management system including an external device in proximity of ICD 101, a remote device in a relatively distant location, and a telecommunication network linking the external device and the remote device. The patient management system provides for access to ICD 101 from a remote location, such as for monitoring patient status and/or adjusting therapies. In one embodiment, telemetry link 103 is an inductive telemetry link. In an alternative embodiment, telemetry link 103 is a far-field radio-frequency telemetry link. Telemetry link 103 provides for data transmission from ICD 101 to external system 102. This may include, for example, transmitting real-time physiological data acquired by ICD 101, extracting physiological data acquired by and stored in ICD 101, extracting therapy history data stored in ICD 101, and extracting data indicating an operational status of ICD 101 (e.g., battery status and lead impedance). Telemetry link 103 also provides for data transmission from external system 102 to ICD 101. This may include, for example, programming ICD 101 to acquire physiological data, programming ICD 101 to perform at least one self-diagnostic test (such as for a device operational status), programming ICD 101 to run a signal analysis algorithm (such as an algorithm implementing a tachyarrhythmia classification method discussed in this document), and programming ICD 101 to deliver pacing and/or cardioversion/defibrillation therapies.

The circuit of ICD 101, including its various elements discussed in this document, may be implemented using a combination of hardware and software. In various embodiments, each element of ICD 101 discussed in this document may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator" includes, among other things, an electronic circuit comparator constructed to perform the only function of a comparison between two signals or a portion of a general-purpose circuit driven by a code instructing that portion of the general-purpose circuit to perform the comparison between the two signals.

Figure 2:
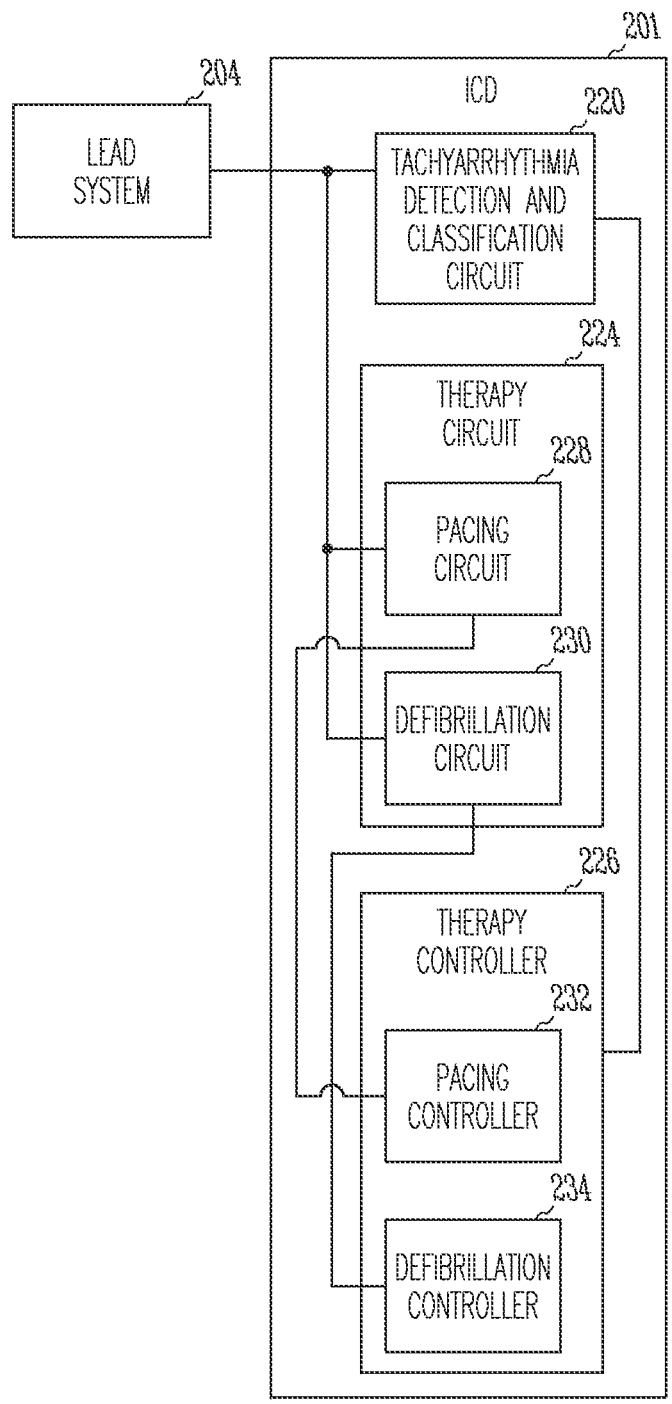
FIG. 2 is a block diagram illustrating an embodiment of an ICD and a lead system of the CRM system.

FIG. 2 is a block diagram illustrating an embodiment of an ICD 201 and a lead system 204. Lead system 204 includes one or more leads such as leads 105 and 110. ICD 201 is a specific embodiment of ICD 101 and includes a tachyarrhythmia detection and classification circuit 220, a therapy circuit 224, and a therapy controller 226. Tachyarrhythmia detection and classification circuit 220 detects and classifies tachyarrhythmia episode using at least one or more intrinsic electrical cardiac signals sensed using lead system 204. In one embodiment, in addition to one or more cardiac signals, tachyarrhythmia detection and classification circuit 220 uses one or more other physiological signals, such as one or more signals indicative of hemodynamic performance, to detect and classify tachyarrhythmia episode. Therapy circuit 224 includes a pacing circuit 228 to deliver pacing pulses to heart 199 through lead system 204 and a defibrillation circuit 230 to deliver cardioversion/defibrillation pulses to heart 199 through lead system 204. Therapy controller 226 includes a pacing controller 232 to control the delivery of the pacing pulses, including ATP pulses, and a defibrillation controller 234 to control the delivery of the cardioversion/defibrillation pulses. Therapy controller 226 selects one or more of pacing and cardioversion/defibrillation therapies based on the classification of the tachyarrhythmia episode. In one embodiment, an ATP therapy is delivered when a detected tachyarrhythmia is classified as a type of tachyarrhythmia known to be treatable by the ATP therapy. If the ATP therapy fails to terminate the tachyarrhythmia, a cardioversion/defibrillation therapy is delivered.

Figure 3:
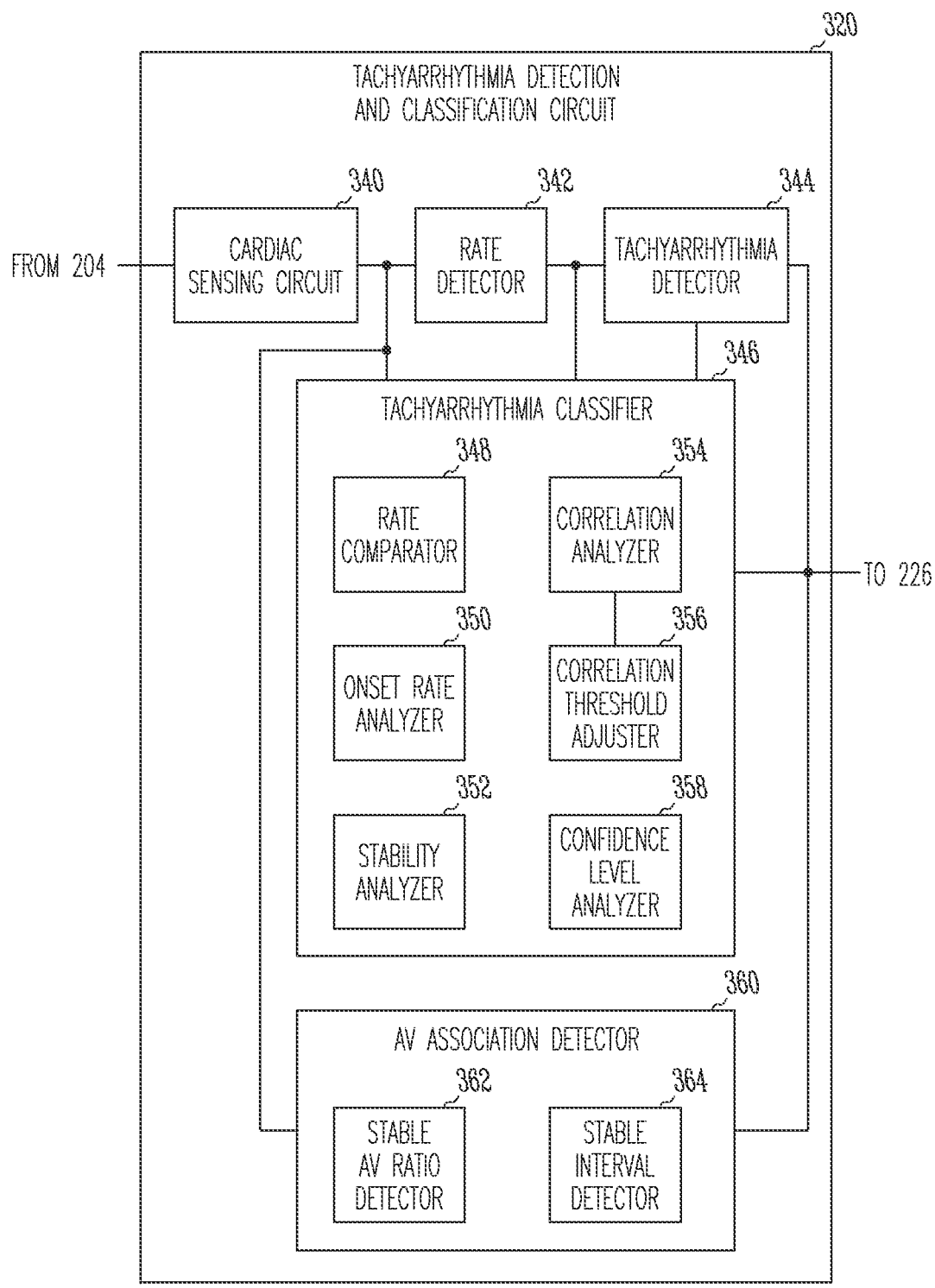
FIG. 3 is a block diagram illustrating an embodiment of a tachyarrhythmia detection and classification circuit of the ICD.

FIG. 3 is a block diagram illustrating an embodiment of a tachyarrhythmia detection and classification circuit 320. Tachyarrhythmia detection and classification circuit 320 is a specific embodiment of tachyarrhythmia detection and classification circuit 220 and includes a cardiac sensing circuit 340, a rate detector 342, a tachyarrhythmia detector 344, a tachyarrhythmia classifier 346, and an AV association detector 360.

Cardiac sensing circuit 340 senses one or more cardiac signals, such as one or more electrograms, through lead system 204. In one embodiment, cardiac sensing circuit 340 is electrically coupled to heart 199 through lead system 204 to sense an atrial electrogram and a ventricular electrogram from the heart. The atrial electrogram includes atrial events, also known as P waves, each indicative of an atrial depolarization. The ventricular electrogram includes ventricular events, also known as R waves, each indicative of a ventricular depolarization.

Rate detector 342 detects one or more heart rates from one or more cardiac signals sensed by cardiac sensing circuit 340. In one embodiment, rate detector 342 detects an atrial rate from the atrial electrogram and a ventricular rate from the ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute.

Tachyarrhythmia detector 344 detects a tachyarrhythmia episode. In one embodiment, a tachyarrhythmia is detected when the ventricular rate exceeds a predetermined tachyarrhythmia threshold rate. In one embodiment, tachyarrhythmia detector 344 detects tachyarrhythmia by determining whether the ventricular rate is within one of a plurality of tachyarrhythmia rate zones each including a predetermined threshold rate. In a specific embodiment, the plurality of tachyarrhythmia rate zones includes a VF rate zone with a VF threshold rate programmable between 130 and 250 bpm, a fast VT rate zone with a fast VT threshold rate programmable between 110 and 210 bpm, and a slow VT rate zone with a slow VT threshold rate programmable between 90 and 200 bpm. In another embodiment, the tachyarrhythmia is detected using a "zoneless tachyarrhythmia detection" method, as discussed in U.S. patent application Ser. No. 11/301,716, "ZONELESS TACHYARRHYTHMIA DETECTION WITH REAL-TIME RHYTHM MONITORING", filed on Dec. 13, 2005, now U.S. Pat. No. 7,702,384, assigned to Cardiac Pacemakers, Inc., which is incorporated herein by reference in its entirety.

Tachyarrhythmia classifier 346 classifies each tachyarrhythmia detected by tachyarrhythmia detector 344. Examples of classification of tachyarrhythmia made by tachyarrhythmia classifier 346 include ventricular fibrillation (VF), ventricular tachycardia (VT), and supraventricular tachycardia (SVT), which includes atrial fibrillation (AF), atrial flutter (AFL), sinus tachycardia (ST), and atrial tachycardia (AT). In one embodiment, a detected tachyarrhythmia is classified as VF when the ventricular rate falls within the VF rate zone, without further analysis by tachyarrhythmia classifier 346. In the illustrated embodiment, tachyarrhythmia classifier 346 includes a rate comparator 348, an onset rate analyzer 350, a stability analyzer 352, a correlation analyzer 354, a correlation threshold adjuster 356, and a confidence level analyzer 358. Rate comparator 348 compares the atrial rate and the ventricular rate to determine whether the atrial rate exceeds, equals, or is lower than the ventricular rate by a predetermined margin. Onset rate analyzer 350 produces an onset rate of the detected tachyarrhythmia and determines whether the detected tachyarrhythmia has a gradual onset or a sudden onset by comparing the onset rate to one or more threshold onset rates. The onset rate is a rate of transition of the ventricular rate from a normal sinus rate to a tachyarrhythmic rate when the detected tachyarrhythmia begins. A gradual onset typically indicates a physiological tachyarrhythmia, such as an ST caused by exercise. A sudden onset typically indicates a pathological tachyarrhythmia. Stability analyzer 352 produces a rate stability parameter indicative of a degree of heart rate variability and determines whether the heart rate is stable by comparing the stability parameter to a stability threshold. In one embodiment, the stability parameter is produced as an average variance of a series of cardiac intervals. In one embodiment, stability analyzer 352 produces a ventricular rate stability parameter and an atrial stability parameter. The ventricular rate stability parameter is indicative of a degree of ventricular rate variability. The atrial stability parameter is indicative of a degree of atrial rate variability. Stability analyzer 352 determines whether the ventricular rate is stable by comparing the ventricular rate stability parameter to a ventricular stability threshold and determines whether the atrial rate is stable by comparing the atrial stability parameter to an atrial stability threshold. In one embodiment, stability analyzer 352 compares the ventricular rate stability parameter and the atrial stability parameter to determine which of the ventricular rate and the atrial rate is more stable. Correlation analyzer 354 analyzes a correlation between a tachyarrhythmic waveform and a template waveform and produces a correlation coefficient representative of that correlation. The tachyarrhythmic waveform includes a segment of a cardiac signal sensed during the detected tachyarrhythmia. The template waveform is recorded during a known cardiac rhythm such as the normal sinus rhythm (NSR). One example for producing such a correlation coefficient, referred to as a feature correlation coefficient (FCC), is discussed in U.S. Pat. No. 6,708,058, "NORMAL CARDIAC RHYTHM TEMPLATE GENERATION SYSTEM AND METHOD," assigned to Cardiac Pacemakers, Inc., which is hereby incorporated in its entirety. In one embodiment, the detected tachyarrhythmia is considered as "correlated" if a correlation coefficient exceeds a correlation threshold and as "marginally correlated" if the correlation coefficient exceeds a marginal correlation threshold that is lower than the correlation threshold. Correlation threshold adjuster 356 allows adjustment of the marginal correlation threshold. Tachyarrhythmia classifier 346 classifies the detected tachyarrhythmia using one or more of the atrial rate, ventricular rate, onset rate, stability parameter, and correlation coefficient.

Confidence level analyzer 358 determines a confidence level associated with a classification of the detected tachyarrhythmia. The confidence level indicates a level of certainty in the classification made by tachyarrhythmia classifier 346. In one embodiment, the confidence level has a value between 0 and 1. In one embodiment, confidence level analyzer 358 determines a confidence level associated with each VT classification of the detected tachyarrhythmia. In one embodiment, the confidence level of classifying the detected tachyarrhythmia as VT is determined using a probabilistic detection technique. An approximate probability of classifying a detected tachyarrhythmia as VT is established by measuring a multidimensional distance of a VT characteristic vector to a composite threshold vector. The distance of a characteristic variable $C_i$ from its threshold $T_i$ is denoted by $\|C_i-T_i\|$, where $\|.\|$ is a generic distance measure. Examples for such a distance measure include Euclidian distance, Mahalanobis distance, and correlation coefficient. The distance measure is then mapped to a scalar $d_i$ ($0<d_i<1$), which represents the confidence level for the characteristic variable $C_i$ to correctly classify the rhythm as VT, i.e., mapping function f: $\|C_i-T_i\| \to d_i$. In one embodiment, the mapping function f takes the form such that $d_i = \exp(-1/\|C_i-T_i\|)$. In one embodiment, $\|C_i-T_i\|$ is scaled to a range such that $d_i$ takes value in full range between 0 and 1, i.e. $d_i = \exp(-1/(a \cdot \|C_i-T_i\|))$, where a is a scaling factor. For example, when $\|C_i-T_i\|$ is scaled to between 0.1 and 100, $d_i$ has the value between 0 and 0.99. In one embodiment, a is determined using an estimate of a reasonable value range of $C_i$ and the threshold $T_i$. For example, if $C_i$ is the ventricular rate stability, then a small stability favors a VT classification. A reasonably estimated lowest value for $C_i$ is 0 ms, so the maximum distance is 20 ms. The scaling factor a is then set to 5 such that when $C_i$ is 0 ms, $d_i$ is 0.99, which indicates a very high confidence for a VT classification. When the difference between $C_i$ and its threshold $T_i$ increases, the distance approaches 1, indicating increased confidence that the VT classification is correct. When the difference between $C_i$ and its threshold $T_i$ decreases, the distance approaches 0, indicating decreased confidence that the VT classification is correct. For all characteristic variables i=1, 2, ... N, the composite distance D is determined as the linear combination of the $d_i$ (i=1, 2, ... N), i.e., $D = \Sigma \alpha_i d_i$, where $\alpha_i$ is the weight for $C_i$, with constraint $0 < \alpha_i < 1$ and $\Sigma \alpha_i = 1$. In one embodiment, $\alpha_i$ is determined using a user's experience with the characteristic variables ($C_i$'s). In another embodiment, $\alpha_i$ is determined as being inversely proportional to the variability of $C_i$. For example, if $C_i$ is the stability value that is calculated as the average of k cardiac cycle lengths, a large variance of $C_i$ suggests a low reliability of the average $C_i$ and hence a smaller $\alpha_i$ is assigned. A VT classification is associated with a relatively low confidence level if the factors used in the classification process, such as the one or more of the atrial rate, ventricular rate, onset rate, stability parameter, and correlation coefficient, exceeds their respective thresholds by a relatively low margin.

AV association detector 360 detects a stable AV association using the atrial depolarizations and ventricular depolarizations sensed by cardiac sensing circuit 340 over a time interval. The stable AV association indicates a substantially stable temporal relationship between the atrial depolarizations and ventricular depolarizations sensed over the time interval. In the illustrated embodiment, AV association detector 360 includes a stable AV ratio detector 362 and a stable interval detector 364. Stable AV ratio detector 362 detects a substantially stable AV ratio, which is a substantially stable ratio of atrial depolarizations to ventricular depolarizations. Stable AV ratio detector 362 indicates the detection of the stable AV association when the substantially stable AV ratio is detected. Stable interval detector 364 detects substantially stable AV or ventriculo-atrial (VA) intervals and indicates the detection of the stable AV association when the substantially stable AV or VA intervals are detected. In one embodiment, whether the AV ratio and the AV or VA intervals are stable are each determined using its variability over time. In one embodiment, the AV ratio is considered substantially stable when the standard deviation of the ratio of the atrial rate to the ventricular rate over consecutive time windows is less than 10% of an average ratio of the atrial rate to the ventricular rate. In one embodiment, the AV or VA interval is considered substantially stable when the standard deviation of the AV or VA interval is less than 10% of an average AV or VA interval.

In one embodiment, tachyarrhythmia classifier 346 classifies the detected tachyarrhythmia using a method discussed below with reference to FIG. 4. The classification of the detected tachyarrhythmia, as well as the various characteristics such as the atrial rate, ventricular rate, onset rate, stability parameter, correlation coefficient, and stable AV association, are used for selecting a suitable anti-tachyarrhythmia therapy, including an ATP mode if the ATP therapy is to be delivered.

In one embodiment, tachyarrhythmia detector 344 performs a detection process that is initiated by a detection of three consecutive fast beats from the ventricular electrogram. In response to the detection of three consecutive fast beats, a tachyarrhythmia detection window is started. The tachyarrhythmia detection window includes ten consecutively detected heart beats starting with and including the three consecutive fast beats. If at least eight out of the ten heart beats in the tachyarrhythmia detection window are fast beats (i.e., the tachyarrhythmia detection window is satisfied), a tachyarrhythmia verification duration is started. Otherwise, the tachyarrhythmia verification duration is not started.

During the tachyarrhythmia verification duration, a moving verification window of ten consecutively detected heart beats is used to determine whether the detected tachyarrhythmia sustains. If at least six out of the ten heart beats in the verification window are fast beats (i.e., the verification window is satisfied), the detected tachyarrhythmia is considered to be sustaining If this verification window fails to be satisfied at any time during the tachyarrhythmia verification duration, the tachyarrhythmia detection is terminated without delivering an anti-tachyarrhythmia therapy. If the detected tachyarrhythmia episode is determined to be sustaining throughout the tachyarrhythmia verification duration, it is classified by tachyarrhythmia classifier 346 to determine the necessity and type of an anti-tachyarrhythmia therapy.

If the detected tachyarrhythmia is classified as a type of tachyarrhythmia for which a ventricular cardioversion/defibrillation therapy is to be delivered, such as a VT episode, the preparation for the delivery of the ventricular cardioversion/defibrillation shock pulse is started. In one embodiment, an ATP therapy is delivered during the preparation for the delivery of the ventricular cardioversion/defibrillation shock pulse. After the preparation for the delivery of the ventricular cardioversion/defibrillation shock pulse is completed, a tachyarrhythmia reconfirmation window of three consecutive heart beats is started, immediately before a scheduled ventricular cardioversion/defibrillation pulse delivery. If at least two out of the three heart beats in the tachyarrhythmia reconfirmation window are fast beats (i.e., the tachyarrhythmia reconfirmation window is satisfied), the detected tachyarrhythmia is considered to be still sustaining, and the ventricular cardioversion/defibrillation pulse is delivered. On the other hand, if the detected tachyarrhythmia is classified as a type of tachyarrhythmia for which a ventricular anti-tachycardia pacing therapy is to be delivered, ventricular anti-tachycardia pacing pulses are delivered without starting the reconfirmation window for checking whether the detected tachyarrhythmia sustains.

If the detected tachyarrhythmia episode is classified as a type of tachyarrhythmia for which no ventricular anti-tachyarrhythmia therapy is needed, such as an SVT episode, a sustained rate duration (SRD) time window may be started, depending on whether it is programmed to be applied. During the SRD, the ventricular rate is monitored to determine whether the tachyarrhythmia episode sustains. If the tachyarrhythmia episode sustains throughout the SRD, the ventricular anti-tachyarrhythmia therapy is delivered when the SRD expires even though the detected tachyarrhythmia episode is classified as an SVT episode. The tachyarrhythmia episode sustains if the ventricular rate remains within the fast or slow VT rate zone. In one embodiment, the tachyarrhythmia episode is considered sustaining when an average ventricular rate (such as an average of ventricular rates detected within a moving window) falls within the fast or slow VT rate zone. In another embodiment, the tachyarrhythmia episode is considered sustaining when a predetermined majority of ventricular beats within a moving detection window are fast beats, such as when at least six out of ten heart beats are fast beats. In one embodiment, if the SRD is programmed to be applied ("ON"), its value is programmable between 10 seconds and 60 minutes, with approximately three minutes as a specific example. The SRD is applied to determine whether a detected tachyarrhythmia needs to be treated because of a sustaining high ventricular rate, after the tachyarrhythmia is classified to be a type that is not to be treated. Thus, the SRD functions as a "safety net" capable of overriding a tachyarrhythmia classification to deliver a therapy. During the SRD, tachyarrhythmia classifier 346 continues to classify the detected tachyarrhythmia and update the classification when necessary. If, for example, the classification changes from SVT to VT during the SRD, a ventricular anti-tachyarrhythmia therapy is to be delivered.

In one embodiment, the AV association and the confidence level are not used in selecting the ATP mode, such as in the method described with reference to FIG. 8. Thus, if ICD 210 does not use the AV association and the confidence level for selecting the ATP mode or any other purpose, tachyarrhythmia detection and classification circuit 320 does not necessarily include confidence level analyzer 358 and AV association detector 360.

Figure 4:
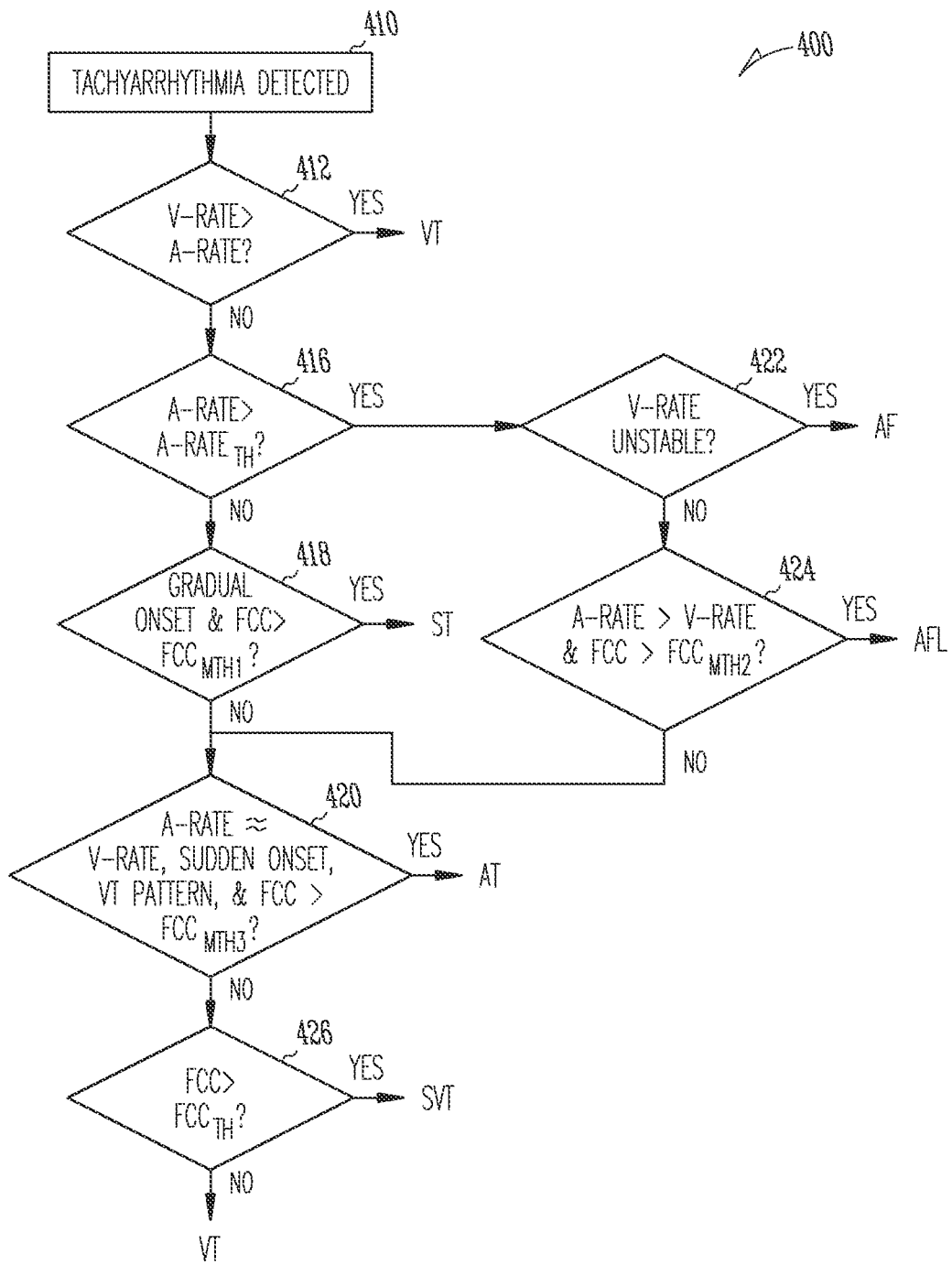
FIG. 4 is a flow chart illustrating a method for classifying detected tachyarrhythmia.

FIG. 4 is a flow chart illustrating a method 400 for classifying a detected tachyarrhythmia. In one embodiment, tachyarrhythmia classifier 346 performs method 400. The atrial rate, ventricular rate, onset rate, stability parameter, correlation coefficient, and various thresholds used in method 400 are detected, produced, or programmed as discussed with reference to FIG. 3 above. For correlation analysis, the template waveform is produced using a cardiac signal sensed during an NSR.

A tachyarrhythmia is detected at 410, when the ventricular rate is within a predetermined tachyarrhythmia rate zone. If the ventricular rate (V-RATE) exceeds the atrial rate (A-RATE) by a predetermined margin at 412, the detected tachyarrhythmia is classified as VT. If the ventricular rate does not exceed the atrial rate by a predetermined margin at 412, the atrial rate is compared to a predetermined threshold atrial rate (A-RATE$_{TH}$) at 416.

If the atrial rate does not exceed the predetermined threshold atrial rate at 416, the onset rate indicates a gradual onset of tachyarrhythmia at 418, and the correlation coefficient (FCC) exceeds a first marginal correlation threshold (FCC$_{MTH1}$) (i.e., FCC falls between FCC$_{MTH1}$ and FCC$_{TH}$) at 418, the detected tachyarrhythmia is classified as ST. ST is a physiologic tachyarrhythmia originated in an SA node when the SA node generates the electrical impulses at a tachyarrhythmic rate. In one embodiment, the first marginal correlation coefficient is programmable between 0.4 and the correlation threshold (i.e., $0.4 \leq FCC_{MTH1} \leq FCC_{TH}$), with approximately 0.8 being a specific example. In one embodiment, the first marginal correlation threshold is set to be lower than the correlation threshold by a predetermined amount, such as approximately 0.2 (i.e., FCC$_{MTH1} \approx$ FCC$_{TH}$−0.2).

If the atrial rate exceeds a predetermined threshold atrial rate at 416, and the ventricular rate is unstable at 422, the detected tachyarrhythmia is classified as AF. If the ventricular rate is stable at 422, the atrial rate exceeds the ventricular rate by a predetermined margin, and the correlation coefficient exceeds a second marginal correlation threshold (FCC$_{MTH2}$) (i.e., FCC falls between FCC$_{MTH2}$ and FCC$_{TH}$) at 424, the detected tachyarrhythmia is classified as AFL. In one embodiment, the second marginal correlation threshold is programmable between 0.4 and the correlation threshold (i.e., $0.4 \leq FCC_{MTH2} \leq FCC_{TH}$), with approximately 0.8 being a specific example. In one embodiment, the second marginal correlation threshold is set to be lower than the correlation threshold by a predetermined amount, such as approximately 0.2 (i.e., FCC$_{MTH2} \approx$ FCC$_{TH}$−0.2).

If the atrial rate approximately equals to the ventricular rate, the onset rate indicates a sudden onset of tachyarrhythmia, the atrial and ventricular events occur in a specified SVT pattern, and the correlation coefficient exceeds a third marginal correlation threshold (FCC$_{MTH3}$) (i.e., FCC falls between FCC$_{MTH3}$ and FCC$_{TH}$) at 420, the detected tachyarrhythmia is classified as AT. In one embodiment, the atrial rate is considered to be approximately equal to the ventricular rate when the difference between the two rates is below 10 bpm. The detection of cardiac event patterns including the SVT pattern is discussed in U.S. patent application Ser. No. 11/276,213, entitled "RHYTHM DISCRIMINATION OF SUDDEN ONSET AND ONE-TO-ONE TACHYARRHYTHMIA", filed on Feb. 17, 2006, now U.S. Pat. No. 7,756,578, assigned to Cardiac Pacemakers, Inc., which is hereby incorporated in its entirety. If these conditions are not met at 420, the correlation coefficient is compared to the correlation threshold (FCC$_{TH}$) at 426. AT is a pathologic tachyarrhythmia that occurs when a biologic pacemaker (focus) in an atrium usurps control of the heart rate from the SA node. In one embodiment, the third marginal correlation threshold is programmable between 0.4 and the correlation threshold (i.e., $0.4 \leq FCC_{MTH3} \leq FCC_{TH}$), with approximately 0.6 being a specific example. In one embodiment, the third marginal correlation threshold is set to be lower than the correlation threshold by a predetermined amount, such as approximately 0.4 (i.e., $FCC_{MTH4} \approx FCC_{TH} - 0.4$).

If the correlation coefficient exceeds the correlation threshold at 426, the detected tachyarrhythmia is classified as SVT. If the correlation coefficient does not exceed the correlation threshold at 426, the detected tachyarrhythmia is classified as VT. In one embodiment, the correlation threshold is programmable between 0.6 and 0.99, with approximately 0.94 being a specific example.

Figure 5:
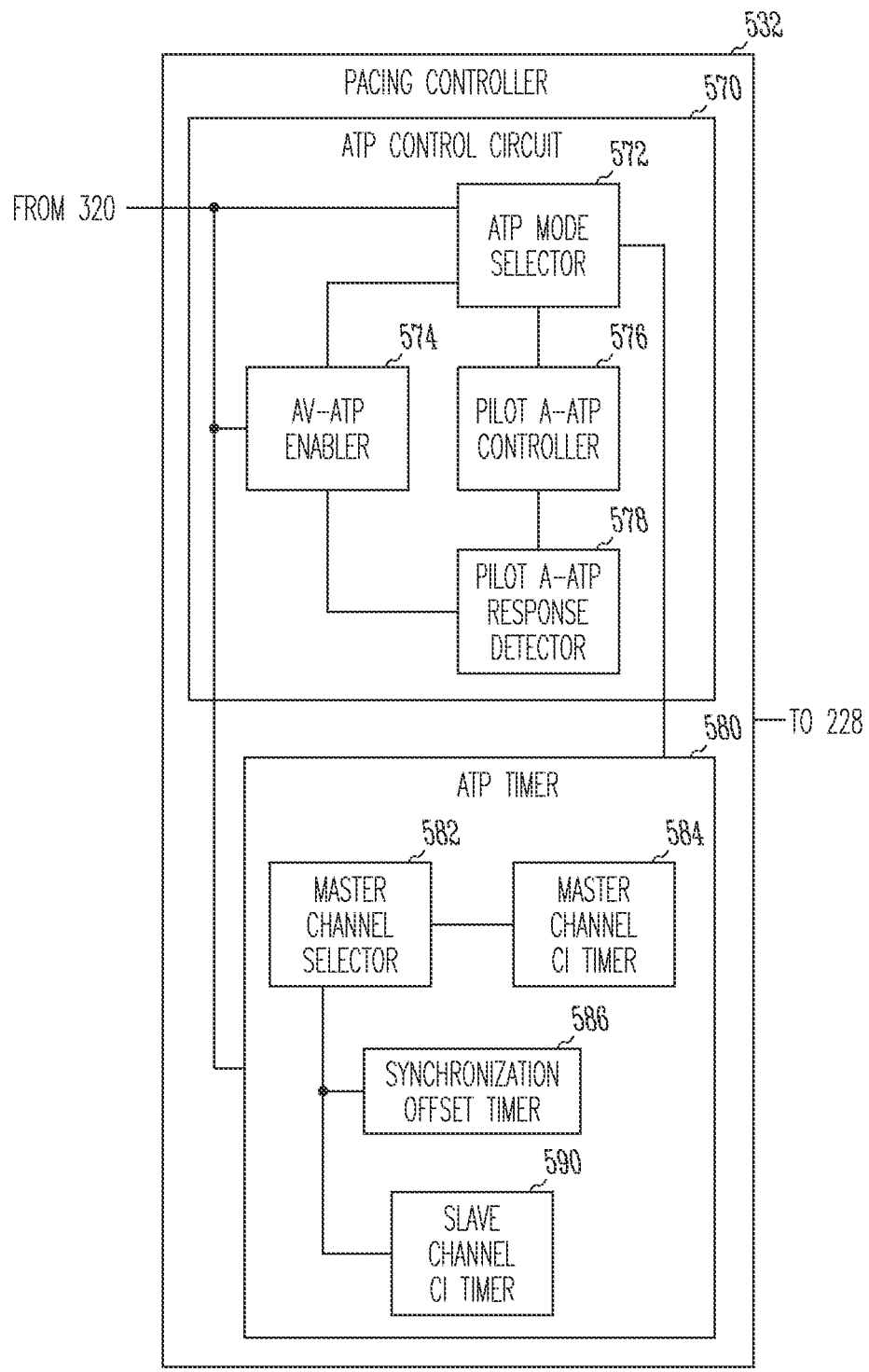
FIG. 5 is a block diagram illustrating an embodiment of a circuit of a pacing controller of the ICD.

FIG. 5 is a block diagram illustrating an embodiment of a circuit of a pacing controller 532, which represents a specific embodiment of pacing controller 232. Pacing controller 532 includes an ATP control circuit 570 that controls delivery of atrial and/or ventricular pacing pulses according to a selected ATP mode. ATP control circuit 570 includes an ATP mode selector 572, an AV-ATP enabler 574, a pilot A-ATP controller 576, a pilot A-ATP response detector 578, and an ATP timer 580.

ATP mode selector 572 selects one of the A-ATP mode, V-ATP mode, and concurrent AV-ATP mode according to one or more specified ATP mode selection criteria. In one embodiment, ATP mode selector 572 selects one of the A-ATP mode, V-ATP mode, and synchronized AV-ATP mode according to a set of ATP mode selection criteria. In one embodiment, ATP mode selector 572 selects the synchronized AV-ATP mode in response to a detection of the stable AV association. In various embodiments, following the detection of a tachyarrhythmia, ATP mode selector 572 also selects the synchronized AV-ATP mode when (i) the detected tachyarrhythmia is classified as VT and the correlation coefficient (produced by correlation analyzer 354) exceeds a specified correlation threshold indicative of a VT origin at ventricular base (high septum), (ii) the atrial rate approximately equals to the ventricular rate and the correlation coefficient exceeds a specified marginal correlation threshold indicative of an origin of tachyarrhythmia near an atrium, (iii) the atrial rate is substantially higher than the ventricular rate, the correlation coefficient exceeds a specified marginal correlation threshold indicative of an origin of tachyarrhythmia near an atrium, and a substantially stable AV ratio is detected, and/or (iv) the detected tachyarrhythmia is classified as VT and the confidence level (produced by confidence level analyzer 364) is below a specified threshold level. If the synchronized AV-ATP mode is not selected, ATP mode selector 572 selects the A-ATP mode when the detected tachyarrhythmia is classified as SVT (AF, AFL, or AT) but not ST, and selects the V-ATP mode when the detected tachyarrhythmia is classified as VT. In one embodiment, the correlation threshold indicative of a VT origin at ventricular base (high septum) is specified as a value approximately between 0.6 and 0.94; the marginal correlation threshold indicative of an origin of tachyarrhythmia near an atrium is specified as a value approximately between 0.6 and 0.8; the specified threshold level for the confidence level is a value approximately between 0.8 and 0.9; the atrial rate is considered to be substantially higher than the ventricular rate when the atrial rate exceeds the ventricular rate by at least a margin specified as a value approximately between 10 and 50 bpm; and the atrial rate is considered to be substantially equal to the ventricular rate when the difference between the two rates is less than a margin specified as a value approximately between 0 and 10 bpm.

In another embodiment, ATP mode selector 572 selects one of the A-ATP mode, V-ATP mode, synchronized AV-ATP mode, and independent AV-ATP mode according to another set of ATP mode selection criteria. When the atrial rate exceeds a threshold atrial rate, and the ventricular rate is below a threshold ventricular rate, ATP mode selector 572 selects the A-ATP mode. When the atrial rate does not exceed the threshold atrial rate, and the ventricular rate exceeds the threshold ventricular rate, ATP mode selector 572 selects the V-ATP mode. When the atrial rate exceeds the threshold atrial rate, the ventricular rate exceeds the threshold ventricular rate, and the ventricular rate is substantially higher than the atrial rate, ATP mode selector 572 selects the V-ATP mode. When the atrial rate exceeds the threshold atrial rate, the ventricular rate exceeds the threshold ventricular rate, and the atrial rate approximately equals the ventricular rate, ATP mode selector 572 selects (i) the synchronized AV-ATP mode when the detected tachyarrhythmia has a sudden onset and the correlation coefficient exceeds the specified marginal correlation threshold indicative of an origin of tachyarrhythmia near an atrium, (ii) the synchronized AV-ATP mode when the detected tachyarrhythmia has a gradual onset and the detected tachyarrhythmia is not classified as ST, (iii) the V-ATP mode when the detected tachyarrhythmia has a sudden onset and the correlation coefficient does not exceed the specified marginal correlation threshold indicative of an origin of tachyarrhythmia near an atrium, and (iv) inhibition of ATP therapy when the detected tachyarrhythmia has a gradual onset and the detected arrhythmia is classified as ST. When the atrial rate exceeds the threshold atrial rate, the ventricular rate exceeds the threshold ventricular rate, and the atrial rate is substantially higher than the ventricular rate, ATP mode selector 572 selects (i) the independent AV-ATP mode when the correlation coefficient exceeds the specified marginal correlation threshold indicative of an origin of tachyarrhythmia near an atrium, and (ii) the V-ATP mode when the correlation coefficient does not exceed the specified marginal correlation threshold indicative of an origin of tachyarrhythmia near an atrium.

AV-ATP enabler 574 allows selection of (or enables pacing at) the concurrent AV-ATP mode according to one or more specified proarrhythmia prevention criteria. In one embodiment, AV-ATP enabler 574 allows selection of (or enables pacing at) the concurrent AV-ATP mode when the ventricular rate falls within a specified rate zone. In a specific embodiment, the rate zone has an upper rate limit programmable between 110 and 180 bpm. AV-ATP enabler 574 disallows selection of (or inhibits pacing at) the concurrent AV-ATP mode when the tachyarrhythmia is classified as sinus tachycardia (ST).

In the illustrated embodiment, pilot A-ATP pacing is delivered to determine whether to inhibit pacing at the synchronized AV-ATP mode. Pilot A-ATP controller 576 controls delivery of a pilot train of A-ATP pulses after the one or more specified ATP mode selection criteria are met. Pilot A-ATP response detector 578 detects a response to the delivery of the pilot train of A-ATP pulses. AV-ATP enabler 574 disallows selection of (or inhibits pacing at) the synchronized AV-ATP mode in response to a detected response satisfying one or more specified synchronized AV-ATP mode inhibition criteria. In one embodiment, pilot A-ATP controller 576 stops the delivery of the pilot train of A-ATP pulses in response to the detected response satisfying one or more specified synchronized AV-ATP mode inhibition criteria. In one embodiment, AV-ATP enabler 574 disallows selection of (or inhibits pacing at) the synchronized AV-ATP mode in response to at least one of the detection of a response indicative of ST and the detection of a response indicative of accelerated atrial and/or ventricular rates. In a specific embodiment, pilot A-ATP controller 576 controls the delivery of the A-ATP pulses using a pacing rate set at approximately 5 to 20% higher than the detected intrinsic atrial rate. Pilot A-ATP response detector 578 indicates a detection of ST if the ventricular rate approximately tracks the atrial rate during the delivery of the pilot A-ATP pulses. In one embodiment, pilot A-ATP response detector 578 considers the ventricular rate to be approximately tracking the atrial rate when the difference between the atrial rate and the ventricular rate is within 5 bpm.

ATP timer 580 times the delivery of the atrial and ventricular pacing pulses. For the capability of timing the delivery of the atrial and ventricular pacing pulses according to the synchronized AV-ATP mode, ATP timer 580 includes a master channel selector 582, a master channel coupling interval (CI) timer 584, a synchronization offset timer 586, and a slave channel coupling interval (CI) timer 590.

During the synchronized AV-ATP mode, master channel selector 582 selects a master AV-ATP channel using the atrial rate stability parameter and the ventricular rate stability parameter produced by stability analyzer 352. In one embodiment, master channel selector 582 selects the channel associated with the highest rate stability as the master AV-ATP channel. The master AV-ATP channel and at least one slave AV-ATP channel are enabled for ATP pulse delivery after the master AV-ATP channel is selected. Master channel coupling interval timer 584 starts a master channel coupling interval ($CI_m$) in response to a detection of intrinsic depolarization in the master AV-ATP channel after the master AV-ATP channel is enabled, and times the a master channel coupling interval. The coupling interval is a time interval between the last detected intrinsic depolarization before the delivery of a burst of ATP pulses and the first pacing pulse of the burst. Delivery of the ATP pulses through the master AV-ATP channel starts upon the expiration of the master channel coupling interval. Synchronization offset timer 586 starts a synchronization offset ($\Delta T_{m-s}$) upon the expiration of the master channel coupling interval, and times the synchronization offset. Slave channel coupling interval timer 590 starts a slave channel coupling interval ($CI_s$) in response to a detection of intrinsic depolarization in the slave AV-ATP channel after the ATP therapy in the synchronized AV-ATP mode is initiated, and times the slave channel coupling interval. Delivery of a burst of ATP pulses through the slave AV-ATP channel starts upon the expiration of the slave channel coupling interval or the expiration of the synchronization offset, whichever occurs later. This is to prevent the pacing pulse delivered through the slave AV-ATP channel from falling into the vulnerable period. In one embodiment, synchronization offset timer 586 calculates the synchronization offset as a fraction of an AV interval measured during the detected tachyarrhythmia when the stable AV association is detected, and calculates the synchronization offset as a fraction of an AV interval measured during a normal sinus rhythm when the stable AV association is not detected. In one embodiment, slave channel coupling interval timer 590 calculates the slave channel coupling interval as a function of the master channel coupling interval when the rate stability parameter of the slave AV-ATP channel indicates a low stability, and calculates the slave channel coupling interval as a function of the measured heart rates of the slave channel when the rate stability parameter of the slave channel indicates a high stability. In one embodiment, the rate stability parameter of each channel is the standard deviation of the cardiac cycle length detected in that channel over a period of time. A high stability is indicated for a channel when the standard deviation computed for that channel does not exceed a stability threshold. A low stability is indicated for a channel when the standard deviation computed for that channel exceeds the stability threshold. In one embodiment, the stability threshold is 20 milliseconds.

During the independent AV-ATP mode, ATP timer 580 times the delivery of the atrial pacing pulses and the delivery of the ventricular pacing pulses individually and independently. In one embodiment, the independent AV-ATP mode is substantially equivalent to the A-ATP mode and the V-ATP mode operating concurrently with independently determined and timed atrial ATP parameters and ventricular ATP parameters. After the independent AV-ATP mode is selected and the ATP therapy is initiated, ATP timer 580 starts an atrial coupling interval ($CI_A$) in response to a detection of intrinsic atrial depolarization and a ventricular coupling interval ($CI_V$) in response to a detection of intrinsic ventricular depolarization. The atrial coupling interval is determined using sensed intrinsic atrial rate. The ventricular coupling interval is determined using sensed intrinsic ventricular rate. Delivery of the atrial pacing pulses starts upon the expiration of the atrial coupling interval. Delivery of the ventricular pacing pulses starts upon the expiration of the ventricular coupling interval.

Figure 6:
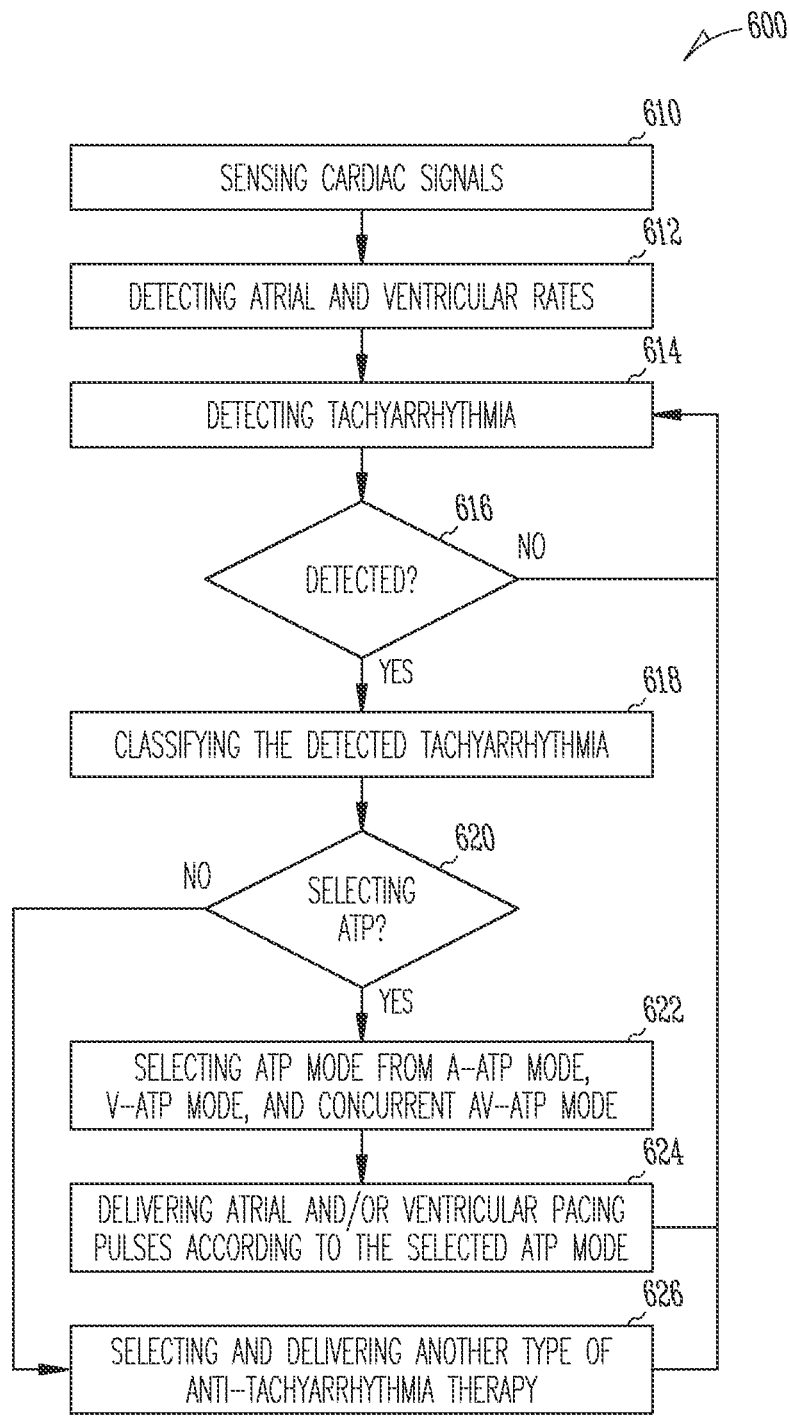
FIG. 6 is a flow chart illustrating an embodiment of a method for controlling ATP.

FIG. 6 is a flow chart illustrating an embodiment of a method 600 for controlling ATP. In one embodiment, method 600 is performed by ATP control circuit 570.

At 610, cardiac signals indicative of atrial and ventricular depolarizations are sensed. At 612, an atrial rate and a ventricular rate are detected using the sensed cardiac signals. At 614, tachyarrhythmia is detected using the ventricular rate and one or more tachyarrhythmia threshold rates. At 618, if a tachyarrhythmia episode is detected at 616, the detected tachyarrhythmia is classified. At 622, if it is determined at 620 that an ATP mode needs to be selected, the ATP mode is selected. In one embodiment, an ATP mode needs to be selected if the ATP therapy is programmed (enabled) and the ventricular rate is below a VF threshold rate. The detected tachyarrhythmia is classified as VF if the ventricular rate exceeds the VF threshold rate. The ATP mode is selected from available modes including the A-ATP mode, V-ATP mode, and concurrent AV-ATP mode using one or more specified ATP mode selection criteria and characteristics of the detected tachyarrhythmia including the classification of the detected tachyarrhythmia. The selection of the ATP mode is further discussed below with reference to FIGS. 7 and 8. At 624, atrial and/or ventricular pacing pulses are delivered according to the selected ATP mode. The control of the ATP delivery is further discussed below with reference to FIG. 9. At 626, if it is determined at 620 that no ATP mode needs to be selected, another type of tachyarrhythmia therapy, such as a cardioversion/defibrillation therapy, is selected using the classification of the detected tachyarrhythmia and delivered to terminate the detected tachyarrhythmia.

Figure 7:
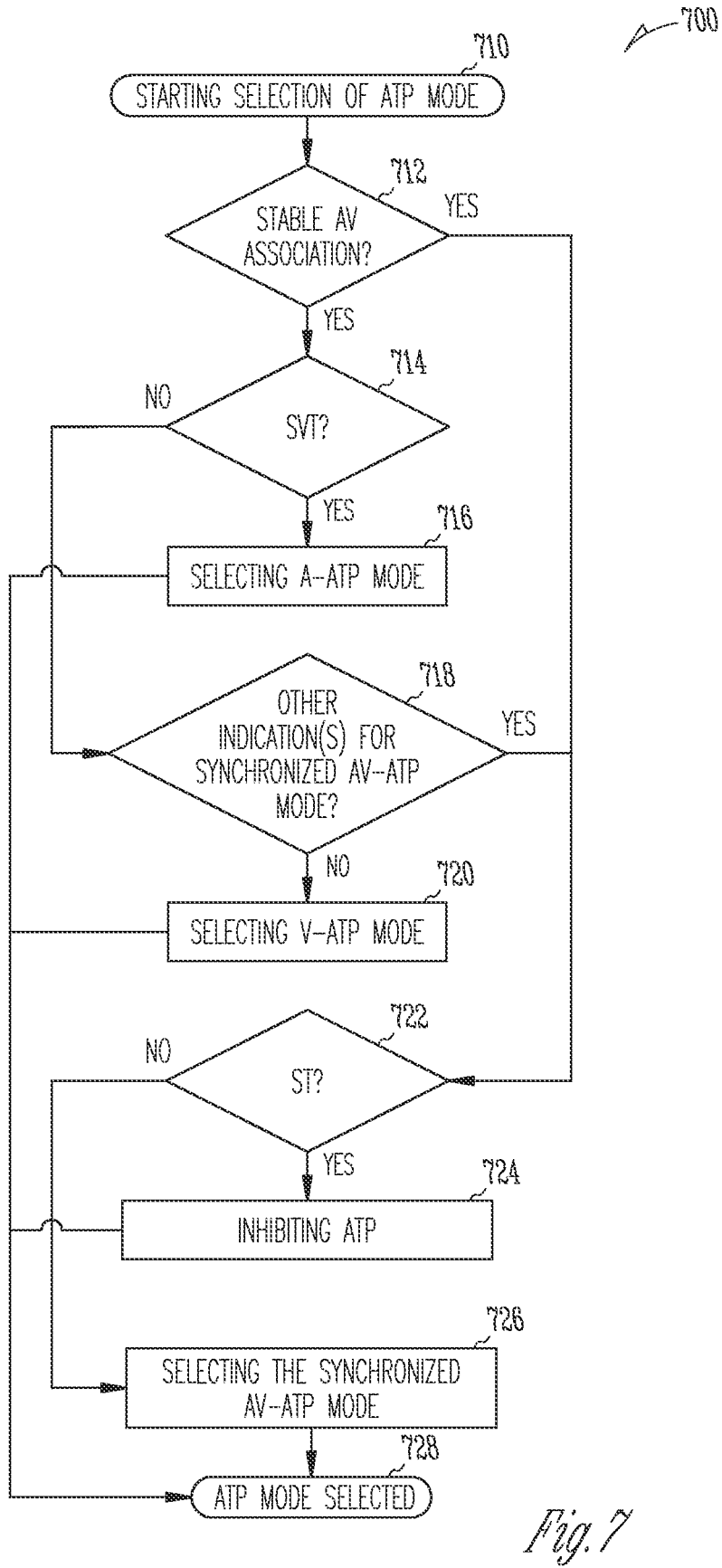
FIG. 7 is a flow chart illustrating an embodiment of a method for selecting an ATP mode.

FIG. 7 is a flow chart illustrating an embodiment of a method 700 for selecting an ATP mode. In one embodiment, method 700 is performed by portions of ATP control circuit 570, including at least ATP mode selector 572 and AV-ATP enabler 574.

At 710, selection of an ATP mode is started. At 712, a stable AV association is being detected using the atrial and ventricular depolarizations sensed over a time interval. The stable AV association is indicative of a substantially stable temporal relationship between the atrial and ventricular depolarizations sensed over the time interval. In one embodiment, the stable AV association is detected when a substantially stable AV ratio is detected. The substantially stable AV ratio is a substantially stable ratio of atrial depolarizations to ventricular depolarizations. In another embodiment, the stable AV association is detected when substantially stable AV or VA intervals are detected. The stable AV association is an indication for ATP therapy at the synchronized AV-ATP mode. If the stable AV association is detected at 712, the synchronized AV-ATP mode becomes the candidate mode subjected to at least another selection criterion at 722.

At 716, the A-ATP mode is selected when the stable AV association is not detected at 712, and the detected tachyarrhythmia is classified as SVT at 714. If the detected tachyarrhythmia is not classified as SVT at 714, it is classified as VT. At 720, the V-ATP mode is selected when the stable AV association is not detected at 712, the detected tachyarrhythmia is not classified as SVT at 714, and no other indication for ATP therapy at the synchronized AV-ATP mode is detected at 718. If there is at least one other indication for ATP therapy at the synchronized AV-ATP mode is detected at 718, the synchronized AV-ATP mode becomes the candidate mode subjected to at least another selection criterion at 722.

In various embodiments, examples for the other indications for ATP therapy at the synchronized AV-ATP mode being detected at 718 include (i) a correlation coefficient exceeds a specified correlation threshold indicative of a VT origin at ventricular base (high septum), (ii) the atrial rate approximately equals to the ventricular rate, and the correlation coefficient produced exceeds a specified marginal correlation threshold indicative of an origin of tachyarrhythmia near an atrium, (iii) the atrial rate is substantially higher than the ventricular rate, the correlation coefficient exceeds a specified marginal correlation threshold indicative of an origin of tachyarrhythmia near an atrium, and a substantially stable AV ratio is detected, and (iv) the detected tachyarrhythmia is classified as VT and the confidence level is below a specified threshold level. The correlation coefficient represents the correlation between a waveform of the cardiac signal sensed during the detected tachyarrhythmia and a template waveform of the cardiac signal sensed during a normal sinus rhythm, such as the correlation coefficient produced by correlation analyzer 354. The confidence level represents the level of confidence in a correct VT classification, such as the confidence level produced by confidence level analyzer 364. These indications indicate an origin of tachyarrhytmia in atria, atrio-ventricular node, or ventricular basal (high-septal) areas or a reentrant loop that covers at least an atrium and a ventricle.

At 724, if the detected arrhythmia is classified as ST at 722, the ATP therapy is inhibited. In one embodiment, a pilot train of A-ATP pulses is delivered in response to the synchronized AV-ATP mode becoming the candidate mode. The response to the delivery of the pilot train of A-ATP pulses is detected. The ATP therapy is inhibited at 724 if the detected response does not satisfy one or more specified synchronized AV-ATP mode inhibition criteria. In one embodiment, the ATP therapy is inhibited at 724 in response to the detection of a response indicative of ST or in response to the detection of a response indicative of accelerated atrial or ventricular rate. At 726, if the detected arrhythmia is not classified as ST at 732, the synchronized AV-ATP mode is selected. At 728, the selection of ATP mode concludes with the ATP mode selected or the ATP therapy inhibited.

Figure 8:
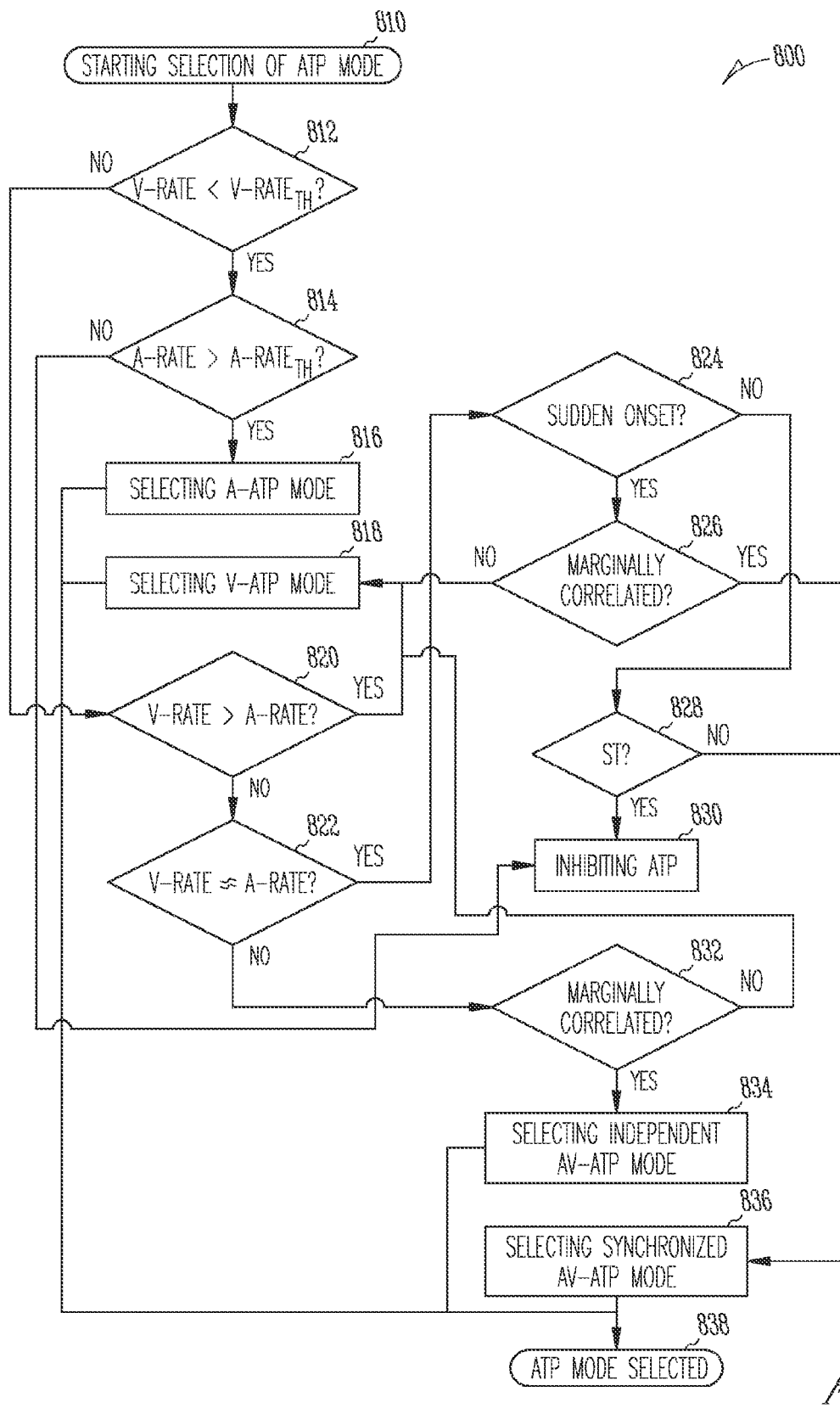
FIG. 8 is a flow chart illustrating another embodiment of a method for selecting an ATP mode.

FIG. 8 is a flow chart illustrating an embodiment of a method 800 for selecting an ATP mode. In one embodiment, method 800 is performed by portions of ATP control circuit 570, including at least ATP mode selector 572 and AV-ATP enabler 574. To perform method 800, ATP mode selector 572 need not receive inputs from confidence level analyzer 358 and AV association detector 360. Consequently, confidence level analyzer 358 and AV association detector 360 are not required in system 100 if only method 800 is performed for ATP mode selection.

At 810, selection of an ATP mode is started. At 816, if the ventricular rate is below a threshold ventricular rate (V-RATE$_{TH}$) at 812, and the atrial rate exceeds a threshold atrial rate (A-RATE$_{TH}$) at 814, and the A-ATP mode is selected. If the atrial rate does not exceed the threshold atrial rate at 814, the ATP therapy is inhibited at 830.

If the ventricular rate is not below the threshold ventricular rate at 812, the atrial rate and the ventricular rate is compared. At 820, whether the ventricular rate is substantially higher than the atrial rate is determined. If the ventricular rate is substantially higher than the atrial rate at 820, the V-ATP mode is selected at 818. At 822, it is determined whether the atrial rate approximately equals to the ventricular rate. If the atrial rate approximately equals the ventricular rate, it is determined whether the detected tachyarrhythmia has a sudden onset, whether the correlation coefficient exceeds a specified marginal correlation threshold indicative of an origin of the detected tachyarrhythmia near an atrium, and whether the detected arrhythmia is an ST. If the detected tachyarrhythmia has a sudden onset at 824, and the correlation coefficient exceeds the specified marginal correlation threshold at 826, the synchronized AV-ATP mode is selected at 836. If the detected tachyarrhythmia has a gradual onset at 824, and the detected arrhythmia is classified as ST at 828, the ATP therapy is inhibited at 830. If the detected tachyarrhythmia has a gradual onset at 824, and the detected arrhythmia is not classified as ST at 828, the synchronized AV-ATP mode is selected at 836. If the detected tachyarrhythmia has a sudden onset at 824, and the correlation coefficient does not exceed the specified marginal correlation threshold at 826, the V-ATP mode is selected at 818.

If the atrial rate does not approximately equal to the ventricular rate (i.e., if the atrial rate is substantially higher than the ventricular rate), it is determined whether the correlation coefficient exceeds the specified marginal correlation threshold. If the correlation coefficient exceeds the specified marginal correlation threshold at 832, the independent AV-ATP mode is selected at 836. If the correlation coefficient does not exceed the specified marginal correlation threshold at 832, the V-ATP mode is selected at 818. At 838, the selection of ATP mode concludes with the ATP mode selected or the ATP therapy inhibited.

Figure 9:
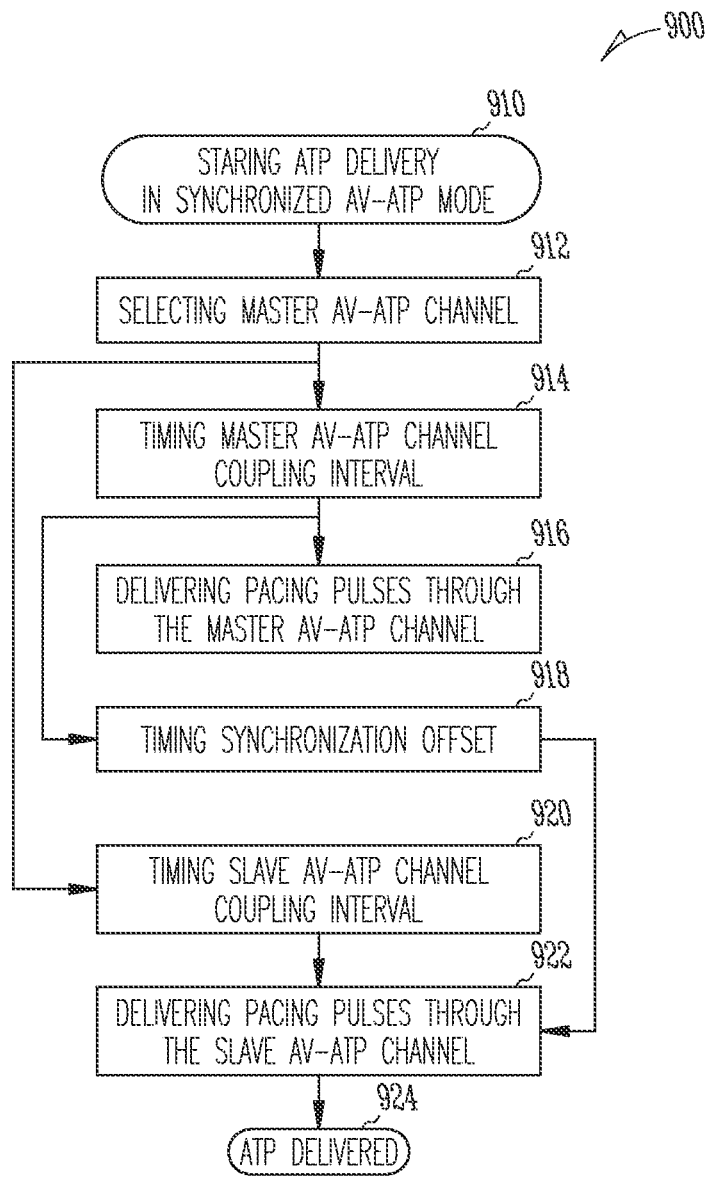
FIG. 9 is a flow chart illustrating an embodiment of a method for timing ATP delivering according to a synchronized AV-ATP mode.

FIG. 9 is a flow chart illustrating an embodiment of a method 900 for timing ATP delivery according to the synchronized AV-ATP mode. In one embodiment, method 900 is performed by ATP timer 580.

At 910, delivery of an ATP therapy in the synchronized AV-ATP mode is started. At 912, a master AV-ATP channel is selected using the atrial rate stability parameter indicative of the stability of the atrial rate and the ventricular rate stability parameter indicative of the stability of the ventricular rate. The channel associated with the highest rate stability is selected as the master AV-ATP channel. The master AV-ATP channel and at least one slave AV-ATP channel are enabled after the master AV-ATP channel is selected.

At 914, a master channel coupling interval (CI$_m$) is timed after the master AV-ATP channel is enabled. The master channel coupling interval starts with an intrinsic depolarization detected through the master AV-ATP channel. At 916, a burst of ATP pulses are delivered through the master AV-ATP channel, with the leading pulse of the burst delivered upon the expiration of the master channel coupling interval.

At 918, a synchronization offset ($\Delta T_{m-s}$) is timed. The synchronization offset starts upon the expiration of master channel coupling interval. In one embodiment, the synchronization offset is calculated as a fraction of an AV interval measured during the detected tachyarrhythmia when the stable AV association is detected by AV association detector 360, and is calculated as a fraction of an AV interval measured during a normal sinus rhythm when the stable AV association is not detected.

At 920, a slave channel coupling interval ($CI_s$) is timed after the slave AV-ATP channel is enabled. The slave channel coupling interval starts with an intrinsic depolarization detected through the slave AV-ATP channel after the slave AV-ATP channel is enabled. In one embodiment, the slave channel coupling interval is calculated as a function of the master channel coupling interval when the rate stability parameter of the slave AV-ATP channel indicates a low stability, and is calculated as a function of the measured heart rates of the slave channel when the rate stability parameter of the slave channel indicates a high stability.

At 922, a burst of ATP pulses are delivered through the slave AV-ATP channel, with the leading pulse of the burst delivered upon the expiration of the slave channel coupling interval or the expiration of the synchronization offset, whichever occurs later. At 924, the delivery of the ATP therapy is concluded.

In one embodiment, the master AV-ATP channel is selected from an atrial channel for delivering the atrial pacing pulses and a ventricular channel for delivering the ventricular pacing pulses. In various embodiments, the master AV-ATP channel is selected as the channel associated with the highest rate stability, among two or more channels each allowing delivery of pacing pulses to a specified cardiac location.

When the stable AV association is detected, using the synchronization offset improves capture for both the master and slave AV-ATP channels by making use of the substantially stable association between the depolarization in these channels. When the master AV-ATP channel is the channel through which atrial pacing pulses are delivered, using the synchronization offset temporally aligns the delivery of the atrial pacing pulses with the delivery of the ventricular pacing pulses, thereby avoiding delivery the atrial pacing pulses into the vulnerable period.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable cardiac rhythm management device, comprising:
   a pacing circuit configured to deliver atrial pacing pulses and ventricular pacing pulses;
   a tachyarrhythmia detection and classification circuit configured to detect a tachyarrhythmia and classify the detected tachyarrhythmia; and
   an anti-tachycardia pacing (ATP) control circuit coupled to the pacing circuit and the tachyarrhythmia detection and classification circuit, the ATP control circuit configured to control delivery of the atrial pacing pulses and the ventricular pacing pulses according to a plurality of ATP modes including a synchronized atrio-ventricular ATP (synchronized AV-ATP) mode during which the atrial pacing pulses and the ventricular pacing pulses are delivered synchronously, the ATP control circuit including an ATP mode selector configured to select an ATP mode from the plurality of ATP modes using one or more specified ATP mode selection criteria and the classification of the detected tachyarrhythmia,
   wherein the tachyarrhythmia detection and classification circuit includes a correlation analyzer configured to produce a correlation coefficient representative of a correlation between a tachyarrhythmic waveform sensed during the detected tachyarrhythmia and a template waveform, and the ATP mode selector is configured to select the synchronized AV-ATP mode from the plurality of ATP modes using the correlation coefficient.

2. The device of claim 1, wherein the tachyarrhythmia detection and classification circuit is configured to sense cardiac signals indicative of atrial depolarizations and ventricular depolarizations and comprises an atrio-ventricular (AV) association detector configured to detect a stable AV association using the atrial depolarizations and ventricular depolarizations sensed over a time interval, the stable AV association indicative of a substantially stable temporal relationship between the atrial depolarizations and ventricular depolarizations sensed over the time interval, and the ATP mode selector is configured to select the synchronized AV-ATP mode from the plurality of ATP modes in response to a detection of the stable AV association.

3. The device of claim 2, wherein the AV association detector comprises a stable AV ratio detector configured to detect a substantially stable AV ratio being a substantially stable ratio of atrial depolarizations to ventricular depolarizations and to indicate the detection of the stable AV association in response to the substantially stable AV ratio being detected.

4. The device of claim 2, wherein the AV association detector comprises a stable interval detector configured to detect substantially stable AV intervals or ventriculo-atrial (VA) intervals and indicate the detection of the stable AV association in response to the substantially stable AV intervals or VA intervals being detected.

5. The device of claim 1, wherein the ATP mode selector is configured to select the synchronized AV-ATP mode in response to the detected tachyarrhythmia being classified as ventricular tachycardia (VT) and the correlation coefficient exceeding a specified correlation threshold indicative of a VT origin at a ventricular base.

6. The device of claim 1, wherein the tachyarrhythmia detection and classification circuit is configured to detect an atrial rate and a ventricular rate, and the ATP mode selector is configured to select the synchronized AV-ATP mode in response to the atrial rate being approximately equal to the ventricular rate and the correlation coefficient exceeding a specified marginal correlation threshold.

7. The device of claim 1, wherein the tachyarrhythmia detection and classification circuit is configured to detect an atrial rate and a ventricular rate and comprises an onset rate analyzer configured to determine whether the detected tachyarrhythmia has a gradual onset indicative of physiological tachyarrhythmia or a sudden onset indicative of pathological tachyarrhythmia, and the ATP mode selector is configured to select the synchronized AV-ATP mode in response to the atrial rate being approximately equal to the ventricular rate, the detected tachyarrhythmia having the sudden onset, and the correlation coefficient exceeding a specified marginal correlation threshold.

8. The device of claim 1, wherein the tachyarrhythmia detection and classification circuit is configured to detect an atrial rate and a ventricular rate and comprises an onset rate analyzer configured to determine whether the detected tachyarrhythmia has a gradual onset indicative of physiological tachyarrhythmia or a sudden onset indicative of pathological tachyarrhythmia, and the ATP mode selector is configured to select the synchronized AV-ATP mode in response to the atrial rate being approximately equal to the ventricular rate, the detected tachyarrhythmia having the gradual onset, and the detected tachyarrhythmia not being classified as sinus tachycardia (ST).

9. An implantable cardiac rhythm management device, comprising:
a pacing circuit configured to deliver atrial pacing pulses and ventricular pacing pulses;
a tachyarrhythmia detection and classification circuit configured to detect a tachyarrhythmia and classify the detected tachyarrhythmia; and
an anti-tachycardia pacing (ATP) control circuit coupled to the pacing circuit and the tachyarrhythmia detection and classification circuit, the ATP control circuit configured to control delivery of the atrial pacing pulses and the ventricular pacing pulses according to a plurality of ATP modes including a synchronized atrio-ventricular ATP (synchronized AV-ATP) mode during which the atrial pacing pulses and the ventricular pacing pulses are delivered synchronously, the ATP control circuit including an ATP mode selector and an atrio-ventricular ATP (AV-ATP) enabler, the ATP mode selector configured to select an ATP mode from the plurality of ATP modes using one or more specified ATP mode selection criteria and the classification of the detected tachyarrhythmia, the AV-ATP enabler configured to disallow selection of the synchronized AV-ATP mode according to one or more specified proarrhythmia prevention criteria.

10. The device of claim 9, wherein the tachyarrhythmia detection and classification circuit is configured to detect a ventricular rate, and the AV-ATP enabler is configured to disallow selection of the synchronized AV-ATP mode in response to the ventricular rate falling outside a specified rate zone.

11. The device of claim 10, wherein the AV-ATP enabler is configured to disallow selection of the synchronized AV-ATP mode in response the tachyarrhythmia being classified as sinus tachycardia (ST).

12. The device of claim 10, wherein the AV-ATP enabler comprises:
a pilot atrial ATP (A-ATP) controller configured to deliver a pilot train of the atrial pacing pulses according to an atrial ATP mode in response to a selection of the synchronized AV-ATP mode; and
a pilot A-ATP response detector configured to detect a response to the delivery of the pilot train of the atrial pacing pulses,
and wherein the tachyarrhythmia detection and classification circuit is configured to detect an atrial rate and a ventricular rate, and the AV-ATP enabler is configured to disallow selection of the synchronized AV-ATP mode in response a detected response indicative of at least one of sinus tachycardia (ST), an accelerated atrial rate, or an accelerated ventricular rate.

13. A method for operating an implantable cardiac rhythm management device, the method comprising:
providing the implantable cardiac rhythm management device with a plurality of anti-tachycardia pacing (ATP) modes for controlling delivery of atrial pacing pulses and ventricular pacing pulses, the plurality ATP modes including a synchronized atrio-ventricular ATP (synchronized AV-ATP) mode during which the atrial pacing pulses and the ventricular pacing pulses are delivered synchronously;
detecting a tachyarrhythmia;
classifying the detected tachyarrhythmia;
producing a correlation coefficient representative of a correlation between a tachyarrhythmic waveform sensed during the detected tachyarrhythmia and a template waveform;
selecting an ATP mode from the plurality of ATP modes using one or more specified ATP mode selection criteria and the classification of the detected tachyarrhythmia, including selecting the synchronized AV-ATP mode in response to the correlation coefficient exceeding a specified correlation threshold; and
controlling the delivery of the atrial pacing pulses and the ventricular pacing pulses from the implantable cardiac rhythm management device according to the selected ATP mode.

14. The method of claim 13, comprising sensing cardiac signals including atrial depolarizations and ventricular depolarizations and detecting a stable atrio-ventricular (AV) association using the atrial depolarizations and ventricular depolarizations sensed over a time interval, the stable AV association indicative of a substantially stable temporal relationship between the atrial depolarizations and ventricular depolarizations sensed over the time interval, and wherein selecting the ATP mode comprises selecting the synchronized AV-ATP mode in response to a detection of the stable AV association.

15. The method of claim 13, comprising determining whether the detected tachyarrhythmia has a gradual onset indicative of physiological tachyarrhythmia or a sudden onset indicative of pathological tachyarrhythmia, wherein selecting the ATP mode comprises selecting the synchronized AV-ATP mode using specified ATP mode selection criteria including whether the detected tachyarrhythmia has a gradual onset or a sudden onset.

16. The method of claim 13, comprising determining a ventricular rate and disallowing selection of the synchronized AV-ATP mode in response to the ventricular rate falls outside of a specified rate zone.

17. The method of claim 13, comprising determining a ventricular rate and disallowing selection of the synchronized AV-ATP mode in response to the detected tachyarrhythmia being classified as sinus tachycardia (ST).

18. The method of claim 13, comprising:
delivering a pilot train of the atrial pacing pulses according to an atrial ATP mode in response to a selection of the synchronized AV-ATP mode;
detecting a response to the delivery of the pilot train of A-ATP pulses; and
disallowing selection of the synchronized AV-ATP mode in response the detected response indicating at least one of a sinus tachycardia (ST), an accelerated atrial rate, or an accelerated ventricular rate.

* * * * *